Figure 1:
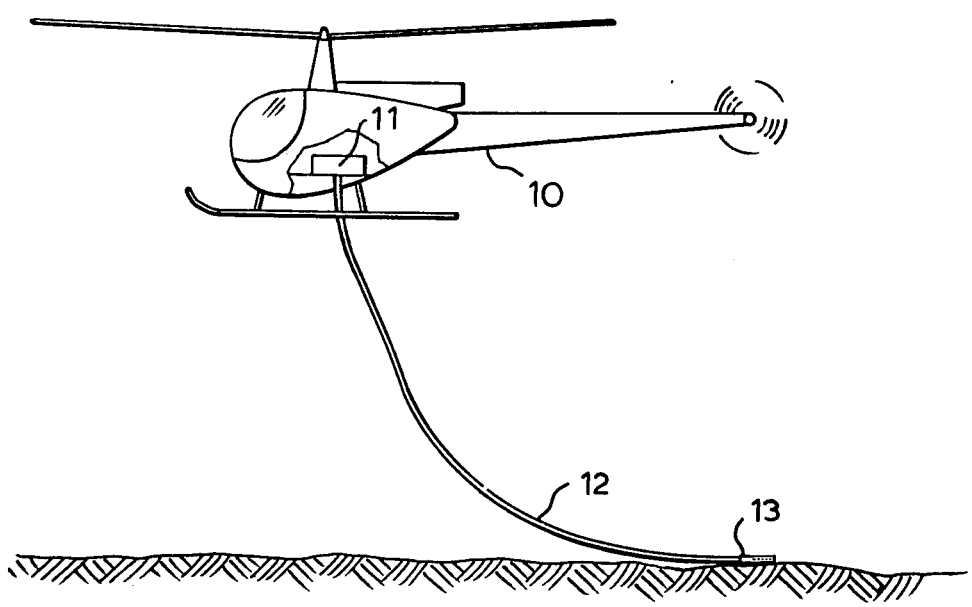

United States Patent [19]

Barringer

[11] 4,192,176

[45] * Mar. 11, 1980

[54] DETECTION OF CONCEALED METALLIFEROUS DEPOSITS, HYDROCARBONS AND EXPLOSIVES

[75] Inventor: Anthony R. Barringer, Golden, Colo.

[73] Assignee: Barringer Research Limited, Rexdale, Canada

[*] Notice: The portion of the term of this patent subsequent to Nov. 8, 1994, has been disclaimed.

[21] Appl. No.: 848,054

[22] Filed: Nov. 3, 1977

Related U.S. Application Data

[63] Continuation-in-part of Ser. No. 679,622, Apr. 23, 1976, Pat. No. 4,056,969.

[51] Int. Cl.² ............................................. G01N 15/00
[52] U.S. Cl. ................................................... 73/28
[58] Field of Search ........... 73/28, 23, 432 R, 432 PS, 73/421 R; 23/230 EP, 232 R, 254 R; 55/270

[56] References Cited

U.S. PATENT DOCUMENTS

| | | | |
|---|---|---|---|
| 2,257,170 | 9/1941 | Howell | 23/230 EP |
| 2,261,764 | 11/1941 | Horvitz | 23/230 EP |
| 2,488,486 | 11/1949 | Worzel | 175/5 |
| 2,717,656 | 9/1955 | Bannister | 340/15.5 |
| 2,918,579 | 12/1959 | Slobod et al. | 23/230 EP |
| 3,078,931 | 2/1963 | Moore | 175/5 |
| 3,327,968 | 6/1967 | Converse | 73/178 |
| 3,364,727 | 1/1968 | Heath | 73/23 |
| 3,477,525 | 11/1969 | Farrell et al. | 175/4 |
| 3,554,005 | 1/1971 | Koblin | 73/28 |
| 3,690,837 | 9/1972 | Witz et al. | 23/232 R |
| 3,730,683 | 5/1973 | Milly | 23/230 EP |
| 3,759,617 | 9/1973 | Barringer | 73/28 |
| 3,768,302 | 10/1973 | Barringer | 73/28 |
| 3,977,479 | 8/1976 | Sainsbury | 73/432 R |

Primary Examiner—Stephen A. Kreitman
Attorney, Agent, or Firm—Rogers, Bereskin & Parr

[57] ABSTRACT

A method of collecting and processing geochemical samples in which particles which are contained on the very surface, or surficial layer of the earth, or of vegetation are collected, and are graded to exclude fine particles below about 50 microns in size.

22 Claims, 8 Drawing Figures

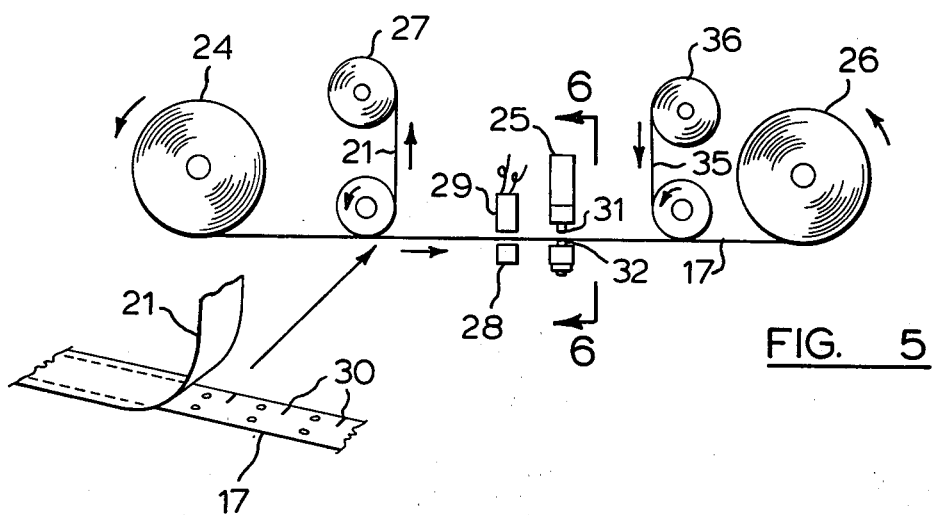
FIG. 5
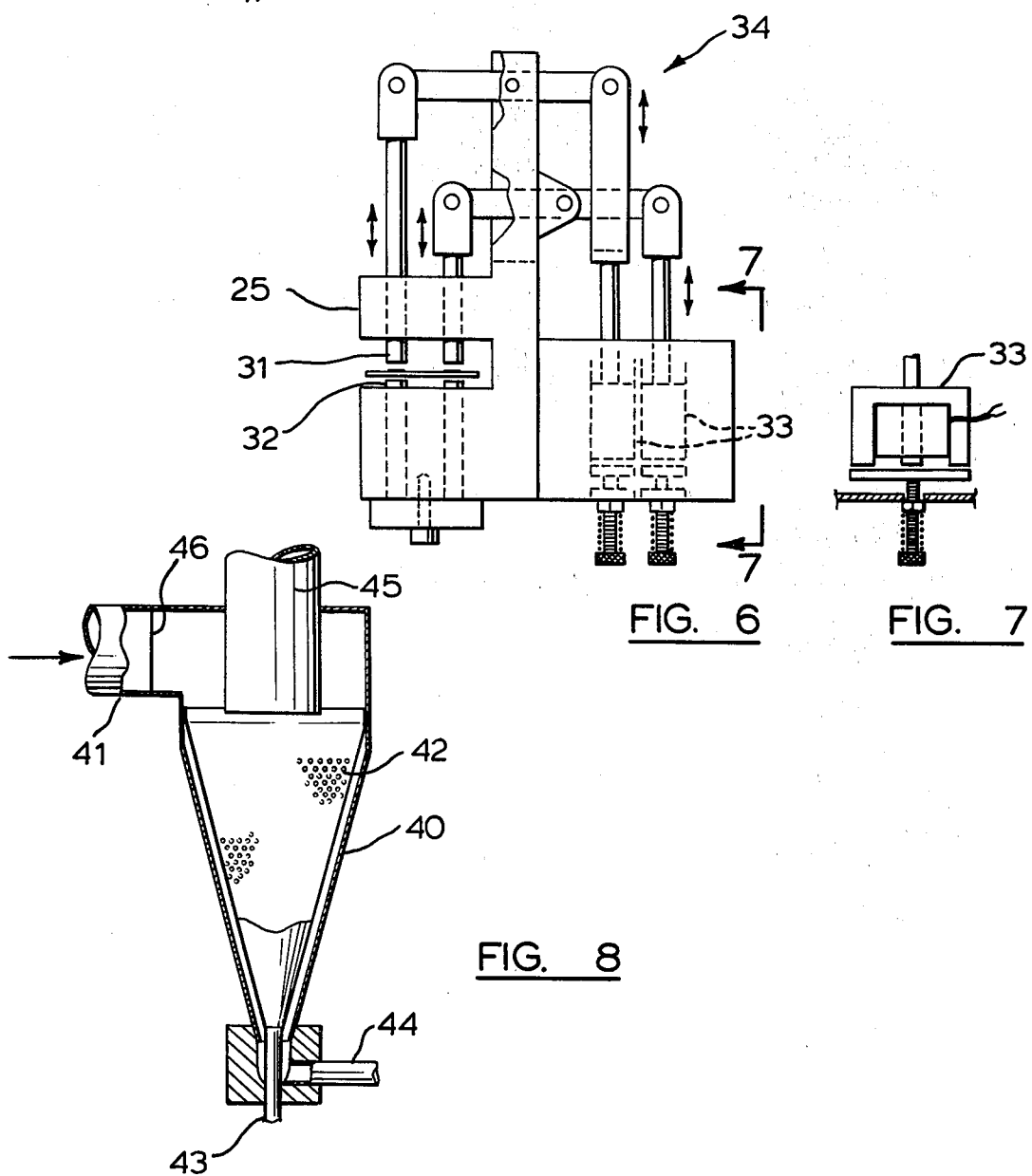
FIG. 6
FIG. 7
FIG. 8

DETECTION OF CONCEALED METALLIFEROUS DEPOSITS, HYDROCARBONS AND EXPLOSIVES

This application is a continuation-in-part of Application Ser. No. 679,622 filed Apr. 23, 1976, now U.S. Patent No. 4,056,969, of Anthony R. Barringer entitled Detection of Concealed Metalliferous Deposits, Hydrocarbons and Explosives.

This invention relates to an improved method and apparatus for geochemical exploration for mineral, hydrocarbon and geothermal deposits, and in particular to an improved method of collecting and processing geochemical samples prior to the analysis thereof.

In conventional geochemical prospecting, samples of rock, soil, vegetation, stream sediments or water are collected and such samples are analyzed for pre-determined elements for the purpose of revealing anomalous geochemical distributions of such elements, related to mineralization or the existence of hydrocarbon deposits. Commonly, the samples are taken in soil at depths of between about 10 cm.–1 m. When samples are taken nearer to the surface, it is usual to discard the top 1 or 2 cm. layer of the soil on the theory that the very surface may be contaminated to some extent, due for example to the presence of animals or deposition of wind swept material. In addition, the collection, storage and analysis of a large number of samples is very time consuming and expensive, so that at present it is practical to take samples only at fairly wide spaced intervals. As a result, it is often difficult to assess the significance of some apparent geochemical anomalies.

The present invention relies on the fact that the earth's surface and to some extent the ocean's surface is covered with a micro-layer of particulate material in contact with the atmosphere that is composed of a mixture of organic and inorganic constituents. It has been found that such particulate material reflects the geochemistry of the underlying soils, and when collected in an appropriate size fraction can provide useful geochemical information. It has also been discovered that coarse particulate material occurring on the surfaces of vegetation and having a biological origin, also exhibits a chemical composition that is closely related to the geochemistry of the underlying soils. Furthermore, the surface particulate material lying on soils and vegetation is in contact with the atmosphere and as a consequence, is exposed to oxidation, weathering and microbiological phenomena that are unique to the atmospheric interface. These phenomena provide certain characteristics that can give high sensitivity in the detection of gaseous fluxes rising from underlying mineralization and hydrocarbon accumulations.

In the present invention, particulates which are contained in the very surface, or surficial layer of the earth, or of vegetation, or water are collected and analyzed. Samples of the surficial layer are taken rapidly, in quick succession, and at relatively low cost. More particularly, particulate or finely divided material comprising the surficial layer of soil, vegetation or water, such as mineral grains, clay minerals, saline evaporative residues, plant fragments, micro-organisms and the like are sampled, for example by applying suction to a tube positioned near to the surface to be sampled.

It was previously considered that the preferred range of particle size was between about 50–200 microns. A particle of about 200 microns in size is considered to be giant, and heretofore it was not considered practicable to collect particles much larger than about 200 microns in size. However, it has now been discovered that giant particles apparently of biological origin are often present on the surfaces of vegetation and they have been found to possess chemical compositions which are closely related to the geochemistry of underlying soils. In addition, giant particles have been found to be particularly useful in wind swept semi-arid regions where fine particles tend to migrate considerable distances and hence tend to make the measurements more diffuse than they would otherwise be. Analysis of such particles heretofore has been a serious problem, however, especially when such particles are stored on a tape, considering that the analyses must be carried out quickly, at low cost, and with good accuracy.

It has now been found that such giant particles may be analysed with good accuracy by crushing the particles prior to their analysis, while they are on the tape, until their size has been reduced sufficiently to facilitate their analysis. It has been found that a vibratory tool applied to the particles for a few seconds is effective to reduce the particle size roughly by a factor of about 10 to 1, and the sample is rendered more homogeneous as well.

Figure 2:
Figure 3:
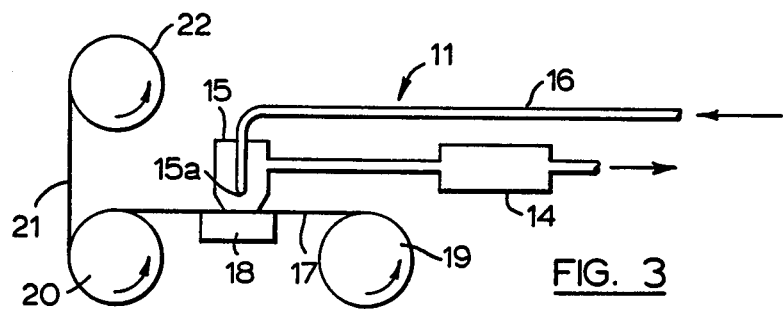
Figure 4:
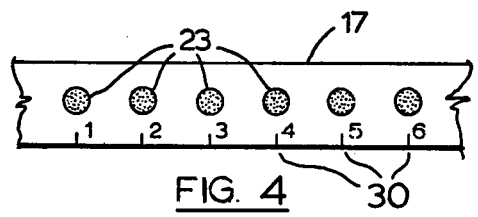

In the drawings,

FIG. 1 is a diagrammatic view showing a helicopter equipped with a suction tube in accordance with a first embodiment of the invention, FIG. 2 is a plan view showing in greater detail the outer end of the tube shown in FIG. 1, FIG. 3 is a diagrammatic view of a preferred form of apparatus for storing collected particulate material, FIG. 4 is a plan view showing a portion of tape used with the embodiment of FIG. 3, FIG. 5 is a diagrammatic view showing a tape on which particles have been deposited, being separated from a cover tape and then being fed past a crushing apparatus, FIG. 6 is a side view of the crushing apparatus shown in FIG. 5, FIG. 7 is an enlarged side view of a vibrator transformer used in the crushing apparatus of FIG. 6, and, FIG. 8 is a diagrammatic side view of a cyclone separator which may be used to separate fine and coarse particles.

Referring to the drawings, and in particular to FIG. 1, apparatus for collecting geochemical samples is shown installed in a helicopter 10. A vacuum pump sampling assembly 11 is supported on shock mounts in the back of the helicopter 10 and is connected to a strong flexible tube 12 which preferably is made of filament wound glass fibres embedded in epoxy resin, of a length of about 8–10 meters, and a diameter of about 3–5 cm. The tube 12 is relatively stiff but is sufficiently resilient that it will yield when it hits an obstruction. The tube 12 terminates in a removable perforated sleeve 13 having a closed outer end as shown in FIG. 2. The sleeve 13 serves the function of sieving out leaves, twigs, etc. and it is formed of a tough, resilient synthetic resin that is resistant to abrasion, such as polycarbonate. It is advisable to form the connection between the tube 12 and the sleeve 13 in such a manner as to facilitate rapid replacement of the sleeve 13. The length of the sleeve 13 is about 1 meter. Particulates sucked through the perforations in the sleeve 13 are fed up the tube 12 inside an inner suction tube (not shown). The particulates reaching the upper end of the suction tube are generally below about 600 microns in size, the maximum size being a function of the size of the openings in the sleeve 13, and the amount of suction applied to the suction tube. Larger particles could be passed up the suction tube by increasing the suction appropriately, but at present there does not appear to be any advantage in collecting particles larger than between about 400–600 microns in size.

The inner end of the suction tube is connected to a cyclone separator 40 as shown in FIG. 8 at an inlet 41. A sieve 46 in the inlet 41 blocks particulates below about 1000 microns in size. The air containing the particulates spins around inside the cyclone 40, and the fine particles are separated from the coarse particles by means of a conical mesh sieve 42 inside the cyclone 40 which preferably is plated with rhodium for abrasion resistance. The coarse particles decend by gravity to outlet pipe 43, and the fine particles are discharged through outlet pipe 44. Excess air leaves the cyclone 40 via outlet pipe 45. The size of the openings of the conical mesh sieve 42 determines the particle size separation. In some areas where there is little wind blown material on the surface, particles above about 50 microns are retained for analysis; in other areas where there is significant risk of contamination by wind swept fine particles, particles above about 200 microns are retained for analysis. The particles emerging from the pipe 43 are the ones which are retained; the fine particles emerging from the pipe 44 are discarded. The pipe 45 is connected to a vacuum pump (not shown) which provides the necessary suction for removing the particles from the surface of the soil or of vegetation, for transporting the particles up the suction tube, and for operating the cyclone 40.

The sampling assembly 11 is shown in FIG. 3 and it consists of a vacuum pump 14 which is connected to an inertial impaction device 15 which in turn is connected to the cyclone outlet pipe 43 by means of a pipe 16. The impaction device 15 is similar to that shown in U.S. Pat. No. 3,868,222 of A. R. Barringer. Air in the pipe 16 carrying particulates is directed through the jet 15a against the surface of the tape 17 the outer surface of which is preferably coated with a suitable adhesive material such as silicone adhesive.

The tape 17 is supported by a block 18 to which is fixed a numbering device which prints a location mark 30 and a number on the tape 17 each time the tape 17 is incrementally advanced. A supply of tape 17 is carried on a reel 19 which feeds the tape 17 past the inertial impaction device 15 onto a pickup reel 20. The adhesive surface of the tape 17 is covered with a cover tape 21 from reel 22. Tape 21 is made of a suitable plastic material which will not adhere strongly to the adhesive surface of the tape 17, such as that sold under the trade mark Teflon. The cover tape 21 protects the particulate samples prior to analysis.

The samples are collected as circular spots 23 on the surface of the tape 17 as shown in FIG. 4 and the tape 17 may be advanced incrementally at equal time periods such as every 10 seconds or equal distance intervals of traverse as determined by distance measuring equipment on the vehicle 10.

A small microphone may be attached to the tube 12 to enable sound levels in the tube 12 to be monitored by the helicopter pilot. By this expedient it is possible to sense when the tube 12 is banging on the ground and/or on vegetation. This arrangement, together with a radio altimeter enables the pilot to obtain a feeling of the performance of the suction system and to maintain appropriate flying height.

Instead of being dragged along the ground, the tube 12 may be drawn across a conopy of trees or of low growing scrub vegetation whereby particulate material carried on the surface of the vegetation is drawn into the sampling assembly 11 through the suction tube. This particulate material comprises organic material derived from the vegetation and contains elements which are indicative of the nutrient elements in the soil in which the vegetation is growing. Thus the method has utility in the exploration of heavily forested regions and other vegetated areas which are difficult to traverse by land vehicles.

It will be understood that although the method of the present invention has been described with reference to a helicopter, the collection apparatus, suitably modified, could be installed in a land vehicle such as a truck or even on a back pack for use by a person on foot. In the latter case, power for the suction pump could be provided by a small gasoline engine.

Prior to the analysis of the particles on the tape 17, the particles are crushed in order to reduce the size of the particles below about 100 microns and preferably below about 50 microns, ideally in the range between about 10–30 microns. This is accomplished by the apparatus shown in FIG. 5, wherein the tape 17 is shown being unwound off a storage reel 24, fed past a crushing apparatus 25, and then wound up on a take-up reel 26. The cover tape 21 is unwound onto a take-up reel 27 upstream of the crushing apparatus 25. A small lamp 28 and a photodetector 29 are positioned in optical alignment on opposite sides of the tape 17, such that the light emanating from the lamp 28 is interrupted by the location marks 30 previously printed on the tape 17. The electrical pulses thereby produced by the photodetector 29 are used to control appropriate circuitry (not shown) which causes the motion of the tape 17 to stop with the spots 23 in proper alignment between hammer 31 and anvil 32 of the crushing apparatus 25. The tape 17 is shown in FIG. 5 as having a pair of spots 23 at each imcremental location on the tape 17, as for example in the case where the particulates were collected in the atmosphere rather than the surface of the earth, using the method disclosed in U.S. Pat. No. 3,970,428 of Anthony R. Barringer dated July 20, 1976. Generally only one spot 23 of particulates is present at each location on the tape 17 when processing surficial particulates, but of course an additional spot 23 could be formed at each location, to be retained perhaps for future analysis.

Each hammer 31 is formed with a head that is slightly larger than each spot 23, allowing for small alignment errors, and the hammers 31 as shown in FIG. 6, are reciprocally driven up and down against the anvils 32 by vibrator transformers 33 which respectively are coupled to the hammers 31 by connecting links generally indicated at 34. The vibrator transformers 33 are adjusted to a convenient frequency, for example 60 Hz. so that the hammers are applied to the spots with a frequency of 60 blows per second. The force of the hammers is adjusted so that the desired amount of crushing is achieved within a reasonable period of time, e.g. 4–6 seconds. A force of between about 6–8 kg. is typical. With such parameters, the particle size is reduced by a factor of roughly 10 to 1, and the particles are crushed into fragments which are smaller than about 100 microns in size, or preferably below 50 microns. A range of 10-30 microns is ideal for the laser analysis method referred to below. After the desired amount of crushing has been achieved, the tape 17 is advanced about half-way between two sets of adjacent spots 23 on the tape and the hammers 31 are again activated, this time against the adhesive coating on the tape 17 since the hammers 31 are now positioned midway between two sets of adjacent spots 23. This serves to clear the hammers 31 thus reducing the risk of contamination when the hammers 31 are again applied to the next set of spots.

As the tape 17 proceeds incrementally past the crushing apparatus 25, a new cover tape 35 is applied to the tape 17 from a reel 36, and the tape 17 with its new cover tape 35 is then wound up on the storage reel 26 and retained for subsequent analysis.

Several alternative methods of analysis of the particulates on the tape can be employed. A preferred method is disclosed in pending United States Application Ser. No. 791,766 filed Apr. 28, 1977 of Anthony R. Barringer wherein the particles are volatized by an intense laser beam and then the volatized matter is excited by a plasma to prepare the matter for spectroscopic analysis. Alternatively, other methods such as X-ray analysis and wet chemical techniques may be employed, although these latter methods at present respectively are not as sensitive or as efficient as the laser method referred to above. In addition, some of the more easily volatized elements and compounds may be analyzed by heating the particulates to drive off the elements or compounds of interest and then analyzing such elements or compounds, for example by using apparatus as shown in U.S. Pat. No. 3,868,222 of Anthony R. Barringer.

The laser analysis method referred to above requires very small amounts of material for each determination, e.g. 5-10 micrograms or even less. However, it is advantageous to collect enough particulate matter (e.g. about 100 micrograms, more or less) so that the adhesive on the tape becomes saturated with particles, i.e. additional particles will not stick to the tape. In such circumstances, the amount of particles collected in each sample will approximately be the same, thus providing a rough degree of normalization for the subsequent analysis.

What I claim is:

1. In a method of collection of geochemical samples wherein samples of surficial particulates of sizes of above about 50 microns are collected and stored and are subsequently analyzed for content of predetermined elements or compounds, said particulates being deposited at predetermined locations in a thin layer on a storage medium, the improvement wherein prior to the analysis of the particulates, the particulates are crushed while on said storage medium to thereby fracture the particulates into fine fragments to facilitate subsequent analysis and to render said samples more homogeneous.

2. A method as claimed in claim 1 wherein said particulates are deposited in groups at spaced-apart intervals on said storage medium and crushed by subjecting them to cyclically repeated hammer blows of predetermined intensity and duration.

3. A method as claimed in claim 2 wherein the duration and force of said hammer blows is sufficient to reduce the size of said particulates to below about 100 microns.

4. A method as claimed in claim 2 wherein said storage medium is an elongated tape, wherein a cover tape is applied to said particulates after they have been collected, and wherein said cover tape is removed prior to the crushing step.

5. A method as claimed in claim 2 wherein the duration and force of said hammer blows is sufficient to reduce the size of said particulates to below about 50 microns.

6. A method as claimed in claim 2 wherein said storage medium is an elongated tape, wherein a cover tape is applied to said particulates after they have been collected, wherein said cover tape is removed prior to the crushing step, and wherein the duration and force of said hammer blows is sufficient to reduce the size of said particulates to below about 50 microns.

7. In a method of collecting geochemical samples, the improvement comprising
    (a) positioning a lower end of an elongated suction tube in proximity to the surface of the earth or of vegetation on said earth surface,
    (b) applying suction to said tube to thereby suck into said tube particles on said earth surface or on said vegetation, and moving said particles along said tube in an airstream,
    (c) filtering said particles to separate particles of sizes of between about 50-1,000 microns in diameter from the remainder of the collected particles, and
    (d) depositing said filtered particles of sizes of between about 50-1,000 microns onto a movable tape in a thin layer, said particles being deposited in groups at predetermined locations and at spaced apart intervals on said tape.

8. A method as claimed in claim 7 wherein the range is between about 200-400 microns.

9. A method as claimed in claim 7 including the additional step of applying a cover tape to said tape after said particulates have been deposited to protect the particulates from contamination.

10. A method as claimed in claim 9 including the additional step of crushing the particulates on said tape to thereby fracture the particulates into fragments of below about 100 microns in size, said cover tape being removed prior to said crushing step.

11. A method as claimed in claim 10 wherein said particulates are reduced in size to below about 50 microns.

12. A method as claimed in claim 7 including the additional step of crushing the particulates on said tape to thereby fracture the particulates into fragments of below about 100 microns in size.

13. Apparatus for use in exploration for mineral, hydrocarbon and geothermal deposits from an aircraft comprising:
    (a) an elongated slender support extending downwardly from the aircraft, said support being relatively stiff but sufficiently resilient to yield upon contacting an obstruction on the surface of the earth.
    (b) a suction tube supported by said support and having an open lower end through which particles on the surface of the earth or on surfaces of vegetation are sucked when said lower end is position proximate to said surfaces,
    (c) means coupled to an inner end of said suction tube for applying suction to said tube to therefore move said particles through said suction tube in a stream of air, and
    (d) means coupled to said suction tube for receiving said airstream containing particles and for grading said particles to remove from said airstream particles above about 1,000 microns in size, and below about 50 microns, the said particles of between about 50–1,000 microns in being retained for subsequent analysis for predetermined elements for compounds.

14. Apparatus as claimed in claim 13 wherein the restricted particles are above about 600 microns in size.

15. Apparatus as claimed in claim 14 wherein the restricted particles are above about 400 microns in size, and said grading means removes particles below about 200 microns in size from said air stream.

16. Apparatus as claimed in claim 15 wherein means positioned downstream of said restricting means is provided for storing said particles on a tape, said tape being positioned in the path of said air stream containing said graded particles and being movable incrementally after a predetermined interval to expose a fresh surface of said tape to said air stream.

17. Apparatus as claimed in claim 14 wherein means positioned downstream of said restricting means is provided for storing said particles on a tape, said tape being positioned in the path of said air stream containing said graded particles and being movable incrementally after a predetermined interval to expose a fresh surface of said tape to said air stream.

18. Apparatus as claimed in claim 13 wherein means positioned downstream of said restricting means is provided for storing said particles on a tape, said tape being positioned in the path of said air stream containing said graded particles and being movable incrementally after a predetermined interval to expose a fresh surface of said tape to said air stream.

19. A method of geochemical exploration comprising:
(a) traversing an area to be explored,
(b) positioning a lower end of an elongated suction tube along the surface of the earth or of vegetation on the surface of the earth in proximity to the surface of the earth or of such vegetation,
(c) applying suction to said tube to thereby suck into said tube samples of particles on said earth's surface or on said vegetation, and moving said particles along said tube in an air stream,
(d) filtering said particles to remove from said air stream particles of sizes of below a selected size,
(e) recording the locations in said area where said samples respectively were collected,
(f) analyzing said samples of collected particles of above said selected size to determine the content of predetermined elements, compounds or micro-organisms, and
(g) correlating data obtained from said analyzing step with said recorded locations to thereby determine the locations where anomalous amounts of predetermined elements, compounds or micro-organisms were collected.

20. A method as claimed in claim 19 including the additional step of depositing said particles onto a movable tape in a thin layer, said particles being deposited in groups at predetermined locations and at spaced apart intervals on said tape, and wherein prior to the deposition of said particles, they are graded in size so that the deposited particles are primarily of sizes of between about 50–600 microns.

21. A method as claimed in claim 20 wherein the range is between about 200–400 microns.

22. A method as claimed in claim 20 including the additional step of applying a cover tape to said tape after said particulates have been deposited to protect the particulates from contamination.

* * * * *